United States Patent

Crabb

[11] Patent Number: 5,524,357
[45] Date of Patent: Jun. 11, 1996

[54] INSTRUMENT CLEANER WITH CONVERGING STEAM JETS

[75] Inventor: James L. Crabb, Germantown, Tenn.

[73] Assignee: Eagle Vision, Inc., Memphis, Tenn.

[21] Appl. No.: 362,833

[22] Filed: Dec. 23, 1994

[51] Int. Cl.⁶ ..................................... F26B 19/00
[52] U.S. Cl. .................. 34/202; 34/389; 134/166 C; 134/170; 15/310
[58] Field of Search ............... 34/201, 202, 389; 15/310; 134/166 C, 169 C, 170, 54, 94.1

[56] References Cited

U.S. PATENT DOCUMENTS

| 3,450,487 | 6/1969 | Wallden . | |
|---|---|---|---|
| 4,414,037 | 11/1983 | Friedheim | 134/35 |
| 4,663,122 | 5/1987 | Sparks | 422/26 |
| 4,803,787 | 2/1989 | Amann | 34/202 |
| 4,949,738 | 8/1990 | Hubbard | 34/202 |
| 5,168,888 | 12/1992 | Aktwasser | 134/199 |
| 5,205,306 | 4/1993 | Peterson | 134/199 |
| 5,213,117 | 5/1993 | Yamamoto | 134/199 |
| 5,240,019 | 8/1993 | Rings | 134/199 |
| 5,249,370 | 10/1993 | Stanger et al. | 34/202 |
| 5,271,893 | 12/1993 | Newman | 422/26 |
| 5,273,395 | 12/1993 | McDermott | 134/199 |
| 5,292,074 | 3/1994 | Clark et al. | 134/199 |

*Primary Examiner*—John T. Kwon
*Attorney, Agent, or Firm*—Jack Lo

[57] ABSTRACT

A surgical instrument cleaner includes a containment chamber with an intake opening on a front thereof and an exhaust vent on a rear thereof. A manifold is positioned in the intake opening, and connected to a steam source. Nozzles arranged around the manifold emit converging steam jets at a single point positioned away from a plane defined by the nozzles. The steam jets are directed rearwardly into the containment chamber, so that they create a front-to-rear airflow between the intake and the exhaust vent. An instrument is positionable at the jet convergence point for cleaning. The airflow carries steam and airborne debris blasted from the instrument safely away from the user.

7 Claims, 3 Drawing Sheets

INSTRUMENT CLEANER WITH CONVERGING STEAM JETS

BACKGROUND OF THE INVENTION

1. Field of the Invention

This invention relates generally to surgical instrument cleaning devices, specifically to a steam jet cleaner for removing surgical debris from instruments.

2. Prior Art

In microsurgery, and especially ophthalmic surgery, extremely accurate and smooth incisions are required. To fill this need, diamond scalpels with superior sharpness and hardness have been developed. Diamond scalpels are extremely expensive, so they are often reused hundreds of times. Stainless steel scalpels are also reused. During surgery, the scalpels are coated with a variety of surgical debris, such as intraocular fluids, proteins, viscoelastic materials, etc. After each use, the scalpels are sterilized in a steam chamber or autoclave.

Autoclaves are shown in U.S. Pat. Nos. 3,450,487 to Wallden (1969); 4,663,122 to Sparks (1987); and 5,271,893 to Newman (1993). These devices sterilize instruments by immersing them in a low velocity flow of high temperature steam within a sealed chamber. The Newman and Sparks devices each includes a single steam inlet (reference numerals 18 and 36, respectively) for its chamber. The Wallden device provides multiple openings and diffuser jets (reference numerals 19 and 20, respectively) that emit parallel jets of steam directed at the top of the chamber for filling it; the parallel jets are not directed at the instruments, which would be positioned on the bottom of the chamber.

Although the autoclaving process sterilizes the surgical debris on the instruments, it does not remove them. Moreover, the high temperature in autoclaving even bakes or hardens the debris on the instruments. As a result, repeated use and autoclaving of surgical instruments cause a buildup of debris that gradually reduces their cutting performance.

U.S. Pat. No. 4,414,037 to Friedheim (1983) shows a device with a single-jet nozzle (reference numeral 14) for sterilizing instruments and blowing away surgical debris. However, the single nozzle produces a diverging steam jet that is only effective when an instrument is held very close—so close that inadvertent contact and damage to the instrument can easily happen. Its single jet can only clean one side of an instrument at a time. In addition, the externally mounted nozzle is pointed in the direction of the user, who can easily be burned by the steam. Furthermore, surgical debris dislodged from the instrument and thrown up in the air by the jet poses a definite health hazard to the user and those nearby. In a typical work area, the steam jet would be pointed at a countertop or floor, which would quickly become contaminated with condensed steam.

In addition to cutting instruments, cannulas are also reused. However, cleaning a cannula is problematic, because the interior of its extremely small channel is virtually impossible to reach with conventional methods and cleaning devices.

OBJECTS AND ADVANTAGES

Accordingly the primary objects and advantages of the present invention are to provide an improved surgical instrument cleaner, a surgical instrument cleaner which effectively removes surgical debris from instruments to prevent buildup and maintain maximum cutting performance, which cleans instruments very quickly, which cleans the interior of cannulas, which removes surgical debris from delicate instruments without damaging them, which is safe to the user, which keeps the work area clean, and which is easy to use. Other objects and advantages of the invention will become apparent from a study of the drawing figures and the following description.

SUMMARY OF THE INVENTION

A surgical instrument cleaner includes a housing with a vented steam containment chamber, a steam source, a circular steam manifold positioned in the chamber, a single-jet nozzle also positioned in the chamber, and a valve for directing steam to either the circular manifold or the single-jet nozzle. The circular manifold includes multiple nozzles emitting converging steam jets to blast away surgical debris simultaneously from all sides of an instrument. The single-jet nozzle includes a luer lock that receives a standard cannula for cleaning the interior thereof. The jets from both the circular manifold and the single-jet nozzle are directed away from the user and into the chamber, which collects the steam and surgical debris for improved worker safety.

DRAWING REFERENCE NUMERALS

| | |
|---|---|
| 10. Housing | 11. Conventional Steam Source |
| 12. Removable Collection Tray | 13. Transparent Cover |
| 14. Containment Chamber | 15. Exhaust Vent |
| 16. Control Valve | 17. Tubing |
| 18. Circular Manifold | 19. Single-Jet Nozzle |
| 20. Tubing | 21. Tubing |
| 22. Intake Opening | 23. Intake Opening |
| 24. Hand Brace | 25. Nozzles |
| 26. Steam Jets | 27. Steam Jet |
| 28. Luer Lock | 29. Cannula Assembly |
| 30. Top Sheet Member | 31. Screws |
| 32. Airflow | 33. Surgical Instrument |

DESCRIPTION—FIG. 1

Figure 1:
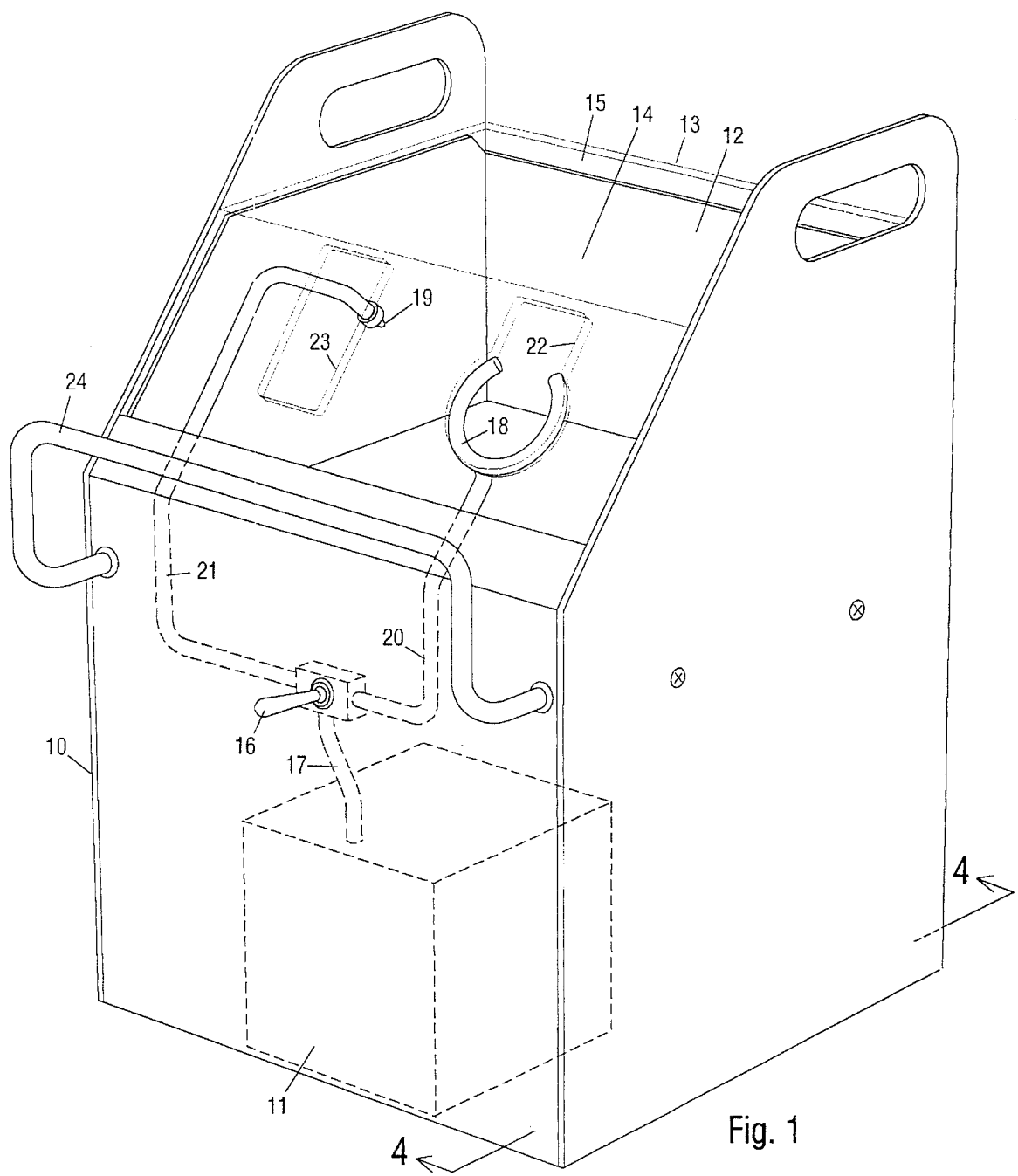
FIG. 1 is a front perspective view of a surgical instrument cleaner in accordance with a preferred embodiment of the invention.

In accordance with a preferred embodiment of the invention shown in the front perspective view in FIG. 1, a surgical instrument cleaner includes an aluminum housing 10 containing a steam source 11, which can be any suitable steam source well known in the art. Housing 10 has an open top that receives a removable, stainless steel collection tray 12, which is covered by a removable, transparent cover 13 made of heat resistant Lexan (a registered trademark of General Electric). Collection tray 12 and cover 13 cooperate to define a containment chamber 14. The rear edge of collection tray 12 has a clipped portion that forms an exhaust vent 15 in conjunction with the rear edge of cover 13.

Steam source 11 is connected to a front-mounted control valve 16 with tubing 17. Valve 16 is manually selectable to direct steam into either a circular manifold 18 or a single-jet nozzle 19 through connecting tubing 20 and 21, respectively. Circular manifold 18 and single-jet nozzle 19 are positioned in intake openings 22 and 23, respectively, on the angled front face of cover 13. A hand brace 24 extends from the front of housing 10. Other necessary controls and instruments for controlling the operation of steam source 11 are well known in the art, so they are not shown.

DESCRIPTION—FIGS. 2A AND 2B

Figure 2A:
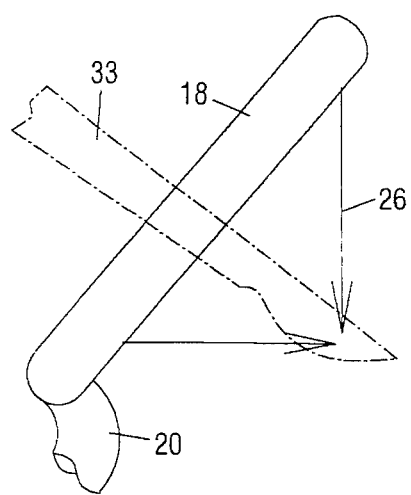
FIG. 2A is a side view of a circular manifold of the surgical instrument cleaner emitting converging steam jets.
Figure 2B:
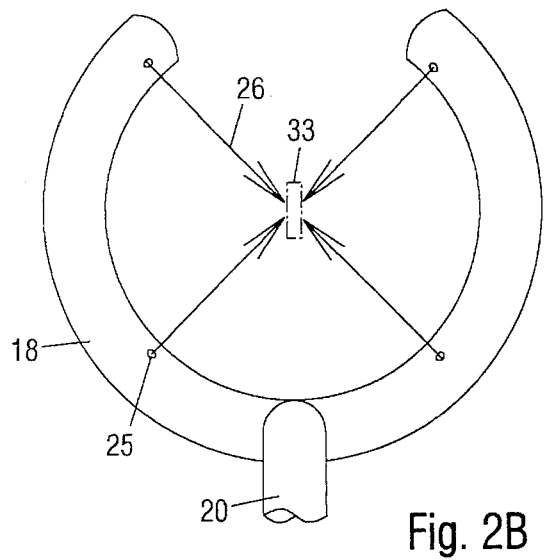
FIG. 2B is a bottom view of the circular manifold.

Circular manifold 18 is shown in side and bottom views in FIGS. 2A and 2B, respectively. Circular manifold 18 has two sealed free ends, and four nozzles 25 (not shown in FIG. 2A) arranged thereon at 90 degree intervals. Nozzles 25 are positioned for directing converging steam jets 26 generally rearwardly at a single point in space. Steam jets 26 can quickly blast away biological debris simultaneously from all sides of a surgical instrument 33. Circular manifold 18 is wide enough to allow an instrument to be maneuvered therein without danger of inadvertent contact. No prior art device includes nozzles oriented for emitting converging jets of steam.

DESCRIPTION—FIG. 3

Figure 3:
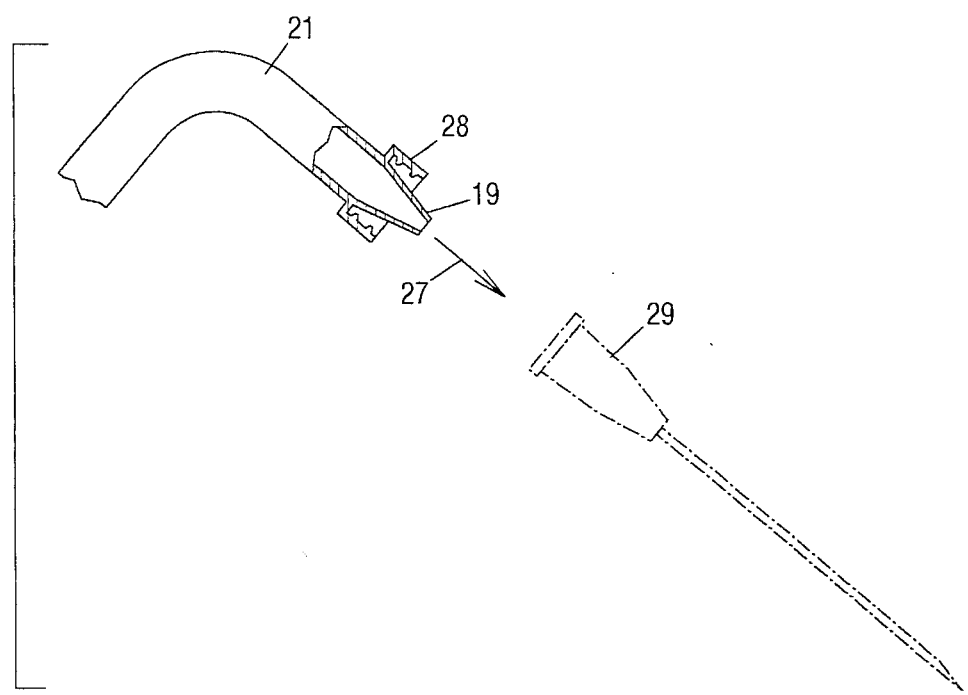
FIG. 3 is a partial sectional side view of a single-jet nozzle of the surgical instrument cleaner.

Nozzle 19 is shown in a partial side sectional view in FIG. 3. Nozzle 19 provides a single, narrow steam jet 27 for cleaning the deep recesses or cavities of instruments (not shown). A luer lock 28—a type of threaded sleeve commonly used in medical devices—is attached around nozzle 19 for removably connecting a conventional cannula assembly 29 for blasting debris from the interior thereof.

DESCRIPTION—FIG. 4

Figure 4:
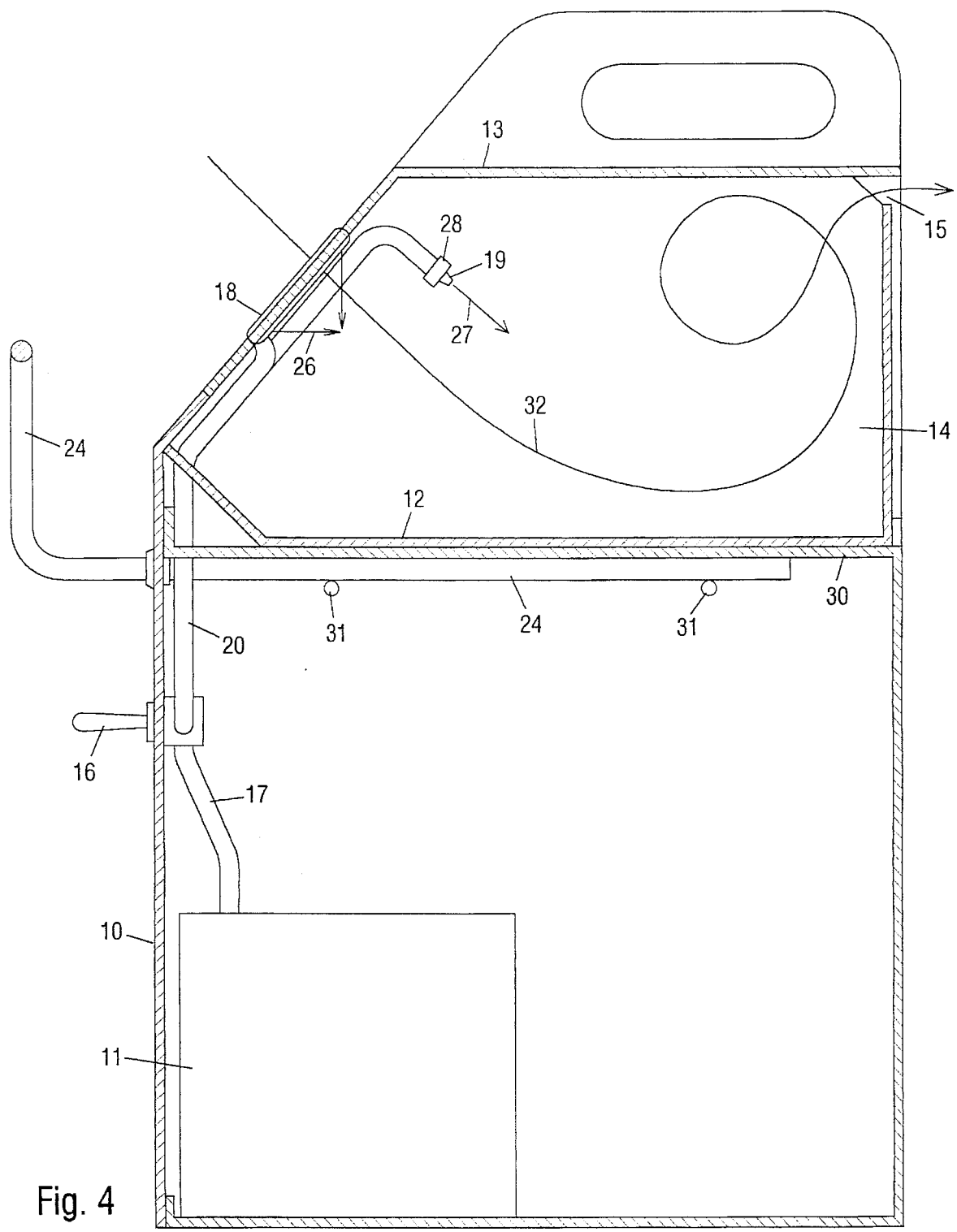
FIG. 4 is a side sectional view of the surgical instrument cleaner taken along line 4—4 in FIG. 1.

As shown in the side sectional view of the surgical instrument cleaner in FIG. 4, each of the two horizontal portions (one shown) of hand brace 24 is slidably fitted between a top sheet member 30 and a pair of screws 31 that extend into each side of housing 10.

In use, control valve 16 is operated to direct steam to either circular manifold 18 or single-jet nozzle 19. A surgical instrument (not shown) is positioned in steam jets 26 or 27 through openings 22 or 23 (FIG. 1), respectively, for blasting away debris to prevent buildup and maintain maximum cutting performance. Hand brace 24 is usable for supporting and steadying a user's hand, and it can be slid in or out of housing 10 to achieve the most comfortable position. A cannula (FIG. 3) can be cleaned by first removing cover 13, connecting it to luer lock 28, and replacing cover 13. After an instrument is cleaned of surgical debris, it can be sterilized in the conventional manner with other devices.

Because steam jets 26 or 27 are pointed rearwardly and downwardly, they create a front-to-rear airflow 32 that enters through intake openings 22 or 23 (FIG. 1), respectively, and exits through vent 15. Airflow 32 positively prevents airborne debris blasted from an instrument and contaminated steam from reaching the user. Furthermore, airborne debris and much of the moisture in the steam are collected in tray 12, so that the work area is kept clean. Tray 12 and cover 13 can both be easily removed from housing 10 for cleaning.

CONCLUSION, RAMIFICATIONS, AND SCOPE

Accordingly the reader will see that I have provided an improved surgical instrument cleaner. It thoroughly blasts away surgical debris from instruments, including the interior of cannulas. It quickly cleans an instrument simultaneously from all sides thereof. It cleans delicate surgical instruments without damaging them. It prevents debris buildup on surgical instruments to maintain top cutting performance. It safely directs steam and airborne surgical debris away from the user. It keeps the work area clean, and it is very easy to use.

Although the above descriptions are specific, they should not be considered as limitations on the scope of the invention, but only as examples of the preferred embodiment. Many other ramifications and variations are possible within the teachings of the invention. For example, the shape of the circular manifold can be changed, as long as the nozzles are generally directed at a single point. A different number of nozzles can be arranged on the manifold. An external steam source can be used. The various components of the steam cleaner can be made of materials other than those described. In addition to cannulas, other types of tubular devices can be attached to the luer lock for cleaning. The steam cleaner can be used for cleaning a variety of other devices in addition to surgical instruments. The cleaner can be adapted for producing jets of liquid. Therefore, the scope of the invention should not be determined by the examples given, but by the appended claims and their legal equivalents.

I claim:

1. An instrument cleaning device, comprising:

a manifold adapted to be connected to a fluid source for receiving a pressurized fluid therefrom; and a plurality of nozzles arranged on said manifold and oriented to emit a plurality of converging fluid jets generally meeting at a single point positioned away from a plane generally defined by said nozzles;

whereby an instrument is positionable at said single point for simultaneously cleaning all sides thereof.

2. An instrument cleaning device, comprising:

a manifold adapted to be connected to a steam source for receiving pressurized steam therefrom; and a plurality of nozzles arranged on said manifold and oriented to emit a plurality of converging steam jets generally meeting at a single point;

whereby an instrument is positionable at said single point for simultaneously cleaning all sides thereof.

3. An instrument cleaning device, comprising:

a containment chamber having an intake opening on a front thereof and an exhaust vent on a rear thereof;

a manifold positioned adjacent said intake opening and adapted to be connected to a fluid source for receiving a pressurized fluid therefrom; and a plurality of nozzles arranged on said manifold and oriented to emit a plurality of converging fluid jets generally meeting at a single point, said nozzles being oriented to direct said fluid jets generally rearwardly into said containment chamber;

whereby an instrument is positionable at said single point for simultaneously cleaning all sides thereof, said fluid jets creating a front-to-rear airflow from said intake opening to said exhaust vent to safely direct said fluid away from a user.

4. An instrument cleaning device, comprising:

a containment chamber defined by a fluid collection tray on a bottom thereof and a transparent cover on a top thereof, said containment chamber having an intake opening on a front thereof and an exhaust vent on a rear thereof:

a manifold positioned adjacent said intake opening and adapted to be connected to a fluid source for receiving a pressurized fluid therefrom; and a plurality of nozzles arranged on said manifold and oriented to emit a plurality of converging fluid jets generally meeting at a single point, said nozzles being oriented to direct said fluid jets generally rearwardly into said containment chamber;

whereby an instrument is positionable at said single point for simultaneously cleaning all sides thereof, said fluid jets creating a front-to-rear airflow from said intake opening to said exhaust vent to safely direct said fluid away from a user, said fluid collection tray collecting residual portions of said fluid from said fluid jets.

5. An instrument cleaning device, comprising:

a containment chamber defined by a fluid collection tray on a bottom thereof and a transparent cover on a top thereof, said containment chamber having an intake opening on a front thereof and an exhaust vent on a rear thereof:

a housing removably receiving said fluid collection tray and said transparent cover; a manifold positioned adjacent said intake opening and adapted to be connected to a fluid source for receiving a pressurized fluid therefrom; and a plurality of nozzles arranged on said manifold and oriented to emit a plurality of converging fluid jets generally meeting at a single point, said nozzles being oriented to direct said fluid jets generally rearwardly into said containment chamber;

whereby an instrument is positionable at said single point for simultaneously cleaning all sides thereof, said fluid jets creating a front-to-rear airflow from said intake opening to said exhaust vent to safely direct said fluid away from a user, said fluid collection tray collecting residual portions of said fluid from said fluid jets.

6. An instrument cleaning device, comprising:

a manifold adapted to be connected to a fluid source for receiving a pressurized fluid therefrom;

a plurality of nozzles arranged on said manifold and oriented to emit a plurality of converging fluid jets generally meeting at a single point;

a single-jet nozzle adapted to be connected to said fluid source for receiving said pressurized fluid therefrom; and a selectable control valve for directing said pressurized fluid to either said manifold or said single-jet nozzle.

7. An instrument cleaning device, comprising:

a manifold adapted to be connected to a fluid source for receiving a pressurized fluid therefrom;

a plurality of nozzles arranged on said manifold and oriented to emit a plurality of converging fluid jets generally meeting at a single point; and a hand brace positioned adjacent said manifold for steadying a user's hand;

whereby an instrument is positionable at said single point for simultaneously cleaning all sides thereof.

* * * * *